(12) United States Patent
Pemberton et al.

(10) Patent No.: US 6,536,294 B1
(45) Date of Patent: Mar. 25, 2003

(54) INSPECTION MACHINE

(75) Inventors: E. Hugh Pemberton, Windsor, CT (US); Stephen M. Giometti, Horseheads, NY (US); Timothy W. Shay, Horseheads, NY (US)

(73) Assignee: Emhart Glass S.A., Cham (CH)

( * ) Notice: Subject to any disclaimer, the term of this patent is extended or adjusted under 35 U.S.C. 154(b) by 809 days.

(21) Appl. No.: 08/856,466

(22) Filed: May 14, 1997

(51) Int. Cl.[7] .............................................. G01M 19/00
(52) U.S. Cl. ................ 73/865.8; 250/223 B; 198/339.1
(58) Field of Search .......................... 73/865.8, 865.9; 250/223 B; 198/339.1, 340, 343.1, 343.2, 345.1–345.3, 346, 346.2, 384

(56) References Cited

U.S. PATENT DOCUMENTS

| 2,596,342 | A | * | 5/1952 | McNutt et al. ............. 209/532 |
| 2,888,127 | A | * | 5/1959 | Ulig ....................... 198/384 X |
| 3,797,632 | A | * | 3/1974 | Riggs ....................... 198/339.1 |
| 4,146,134 | A | * | 3/1979 | Keen et al. ........... 250/223 B X |
| 4,200,183 | A | | 4/1980 | Riggs ......................... 198/648 |
| 4,218,913 | A | * | 8/1980 | Comfort ..................... 73/45.2 |
| 4,278,173 | A | * | 7/1981 | Pembenton et al. ......... 209/522 |
| 4,820,972 | A | * | 4/1989 | Scott et al. ................. 324/687 |
| 4,915,237 | A | * | 4/1990 | Chang et al. ........... 209/526 X |
| 4,955,227 | A | * | 9/1990 | Fujita et al. .................. 73/104 |
| 4,996,658 | A | * | 2/1991 | Buke ...................... 324/671 X |
| 5,723,797 | A | * | 3/1998 | Dimmick et al. .......... 73/865.8 |

FOREIGN PATENT DOCUMENTS

| DE | 3611494 | * | 10/1987 | |
| GB | 754911 | | 8/1956 | |
| GB | 1552994 | * | 9/1979 | |
| SU | 753735 | * | 8/1980 | .............. 198/339.1 |

OTHER PUBLICATIONS

Multi–Steton Products Brochure by Emhart Glass Entitled Total Inspection Machine System, 6 pages, Published by Feb. 1999.*

* cited by examiner

*Primary Examiner*—Thomas P. Noland
(74) *Attorney, Agent, or Firm*—Spencer T. Smith

(57) ABSTRACT

A machine for inspecting glass bottles comprising an elliptical first conveyor having parallel linear front and rear portions. Bottles are displaced sequentially along the linear front portion of the elliptical first conveyor by a first cam and bottles are sequentially displaced along the linear rear portion of the elliptical first conveyor by a second cam. Inspection stations bottles are located along both the front and rear linear portions. A second conveyor delivers bottles to the elliptical conveyor proximate the start of the first cam, and a third conveyor receives bottles from the elliptical conveyor proximate the end of the second cam.

7 Claims, 1 Drawing Sheet

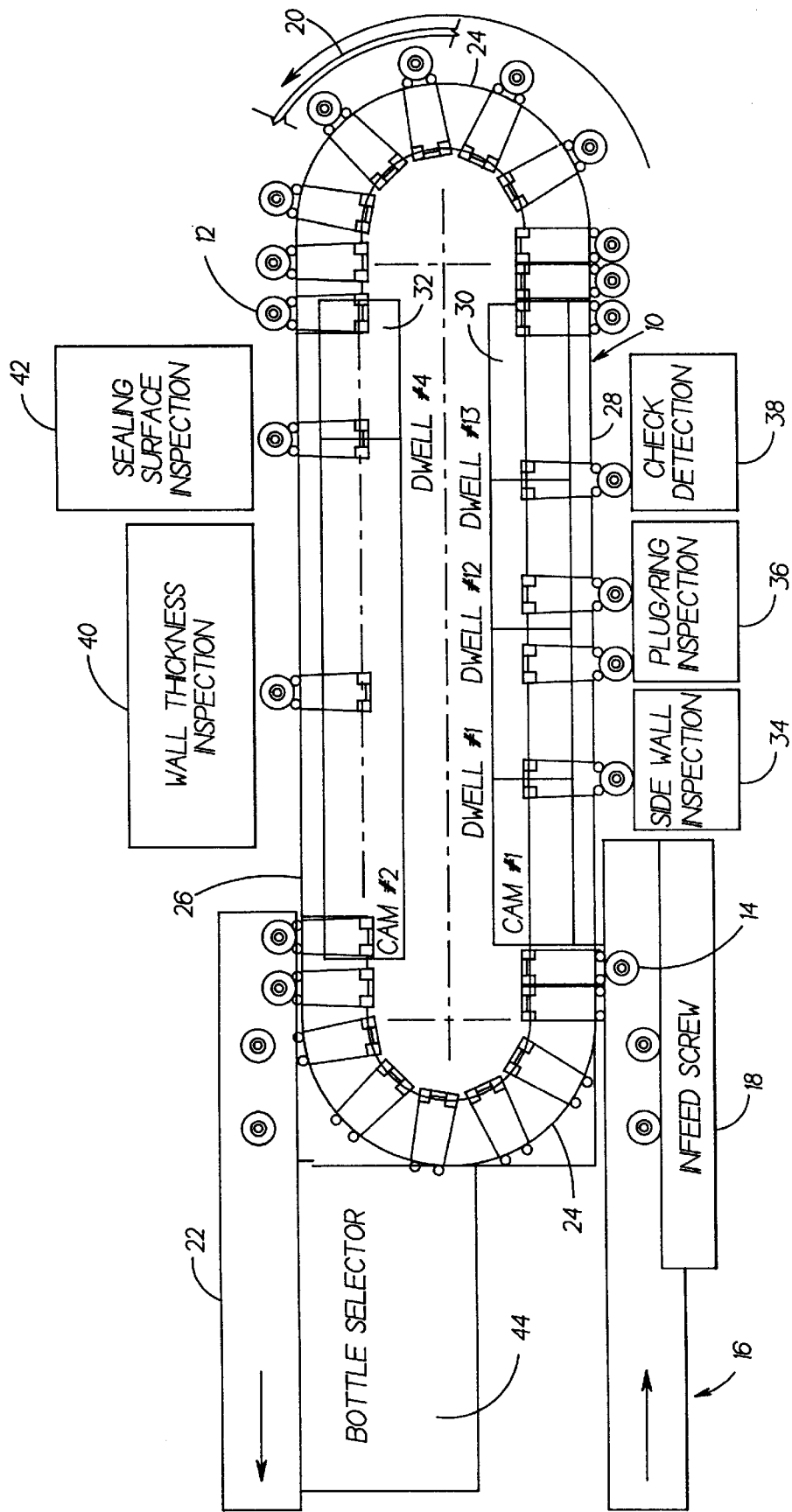

INSPECTION MACHINE

The present invention relates to machines for inspecting glass containers such as bottles.

BACKGROUND OF THE INVENTION

Glass bottles formed in an I.S. machine may have one or more defects. The top surface of the bottle may not be smooth and as a result the cap may not seal the contents of the bottle. The opening of the bottle may be too small or the O.D. of the finish may be too large. And there may be a great variety of defects in the glass that make the bottle unacceptable. A number of inspection machines have been developed to identify these defects. In one design, which is disclosed in U.K. Patent No. 1,552,994, individual carriages are displaced around a closed elliptical loop. Bottles to be inspected are delivered by a first conveyor to the start of one side of the elliptical path and are transferred to these carriages. Each bottle is then carried along this side past an inspection station, and, at the end of the side, is transferred to a second conveyor which is in line with the first conveyor. Such machines have now been developed to have as many as six or seven inspection stations along the side connecting the conveyors. As the number of inspection stations increases so, too, does the length of the machine.

OBJECT OF THE INVENTION

It is an object of the present invention to make this machine more productive.

Other objects and advantages of the present invention will become apparent from the following portion of this specification and from the accompanying drawings which illustrate in accordance with the mandate of the patent statutes a presently preferred embodiment incorporating the principles of the invention.

BRIEF DESCRIPTION OF THE DRAWINGS

The sole FIGURE is a schematic presentation of the invention.

BRIEF DESCRIPTION OF THE PREFERRED EMBODIMENT

The inspection machine has an elliptical conveyor 10 which supports a plurality of bottle holding carriages 12 which capture individual bottles 14 supplied to the machine by an supply conveyor 16 which includes an feed screw 18 for properly spacing the bottles. A captured bottle is held against its carriage by a guide rail 20 which extends from the supply conveyor to the discharge conveyor 22. The elliptical conveyor 10 has semicircular end portions 24 which join parallel rear 26 and front 28 portions. The front portion has a cam 30 (cam#1) and the rear portion has a cam 32 (cam#2). Each cam functions to carry the individual carriages from one end portion to the other (the carriages are packed around each end). Located along the first cam 30 are three inspection stations (mechanisms): sidewall inspection 34, plug/ring inspection 36, and check detection 38 and the first cam defines dwells (dwell#1, dwell#2, dwell#3) at these inspection stations. Located along the second cam 32 are two inspection stations: wall thickness inspection 40 and sealing surface inspector 42 and the second cam defines a forth dwell (dwell#4) at the sealing surface inspector and defines constant carriage velocity across the wall thickness inspection station. When a bottle leaves the second cam it is deposited on the discharge conveyor 22 which may include a bottle selector 44 for removing selected bottles for additional study.

What is claimed is:

1. A machine for inspecting glass bottles comprising an elliptical first conveyor having parallel linear front and rear portions, means for displacing bottles sequentially along the linear front portion of said elliptical first conveyor including a first cam, means for displacing bottles sequentially along the linear rear portion of said elliptical first conveyor including a second cam, means for inspecting bottles displaced along said front and rear linear portions including at least one inspection station located proximate said front linear portion, and at least one inspection station located proximate said rear linear portion, a second conveyor for delivering bottles to said linear front portion of said elliptical conveyor proximate a start of said first cam, and a third conveyor for receiving bottles from said linear rear portion of said elliptical conveyor proximate an end of said second cam.

2. A machine for inspecting glass bottles according to claim 1, wherein said second and third conveyors are parallel.

3. A machine for inspecting glass bottles according to claim 2, wherein said at least one inspection station is proximate said first cam and includes a sidewall inspection mechanism.

4. A machine for inspecting glass bottles according to claim 3, wherein said at least one inspection station proximate said first cam further includes a plug/ring inspection mechanism.

5. A machine for inspecting glass bottles according to claim 4, wherein said at least one inspection station proximate said first cam further includes a check detection mechanism.

6. A machine for inspecting glass bottles according to claim 3, wherein said at least one inspection station is proximate said second cam and includes a wall thickness inspection mechanism.

7. A machine for inspecting glass bottles according to claim 6, wherein said at least one inspection station proximate said second cam further includes a sealing surface inspector mechanism.

\* \* \* \* \*